US00PP13431P2

(12) United States Plant Patent
Berry

(10) Patent No.: US PP13,431 P2
(45) Date of Patent: Dec. 31, 2002

(54) ***TAXODIUM DISTICHUM* PLANT NAMED 'SOFINE'**

(75) Inventor: James Bryan Berry, Daphne, AL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 10/020,117

(22) Filed: Dec. 18, 2001

(51) Int. Cl.[7] ..... A01H 5/00
(52) U.S. Cl. ..... Plt./213
(58) Field of Search ..... Plt./213

*Primary Examiner*—Bruce R. Campell
*Assistant Examiner*—A Para

(57) ABSTRACT

A new and distinct variety of *Taxodium distichum* plant named 'Sofine', characterized by its uniform growth habit, foliage size, and foliage color.

2 Drawing Sheets

BACKGROUND OF THE INVENTION

The present invention relates to a new and distinct cultivar of Taxodium, botanically known as *Taxodium distichum*, and hereinafter referred to by the cultivar name 'Sofine'. This new Taxodium variety was discovered by James Bryan Berry in November, 1991 as an openly pollinated seedling in a group of unnamed, unpatented *Taxodium distichum* plants at Plant Development Services Inc. in Loxley, Ala. The value of this new cultivar lies in its uniform growth habit, foliage size, and foliage color. The new variety has retained many of the outstanding attributes of its parent species, in particular its tolerance of insects and disease, which makes it adaptable to culture in the Sunbelt states.

Asexual propagation of the new plant by cuttings has been under Mr. Berry's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. A uniformly dense, upright and pyramidal growth habit 50 to 70' high and 20 to 30' wide.

2. Uniformly shaped foliage.

3. Attractive bright yellow-green immature foliage in the spring darkens to a soft green and finally a golden-brown fall color.

4. Fast growth rate under normal fertilization and moisture conditions.

5. Easily propagated with semi-hardwood cuttings in late spring through the summer.

6. Tolerates full sun to light shade.

7. Good specimen plant.

8. Very adaptable to wet, dry and well-drained soil conditions.

9. Effectively used in groupings around lakes and rivers.

10. Attractive reddish-brown bark.

11. Exceptionally wind firm.

12. Hardy to Zone 5.

DESCRIPTION OF THE DRAWINGS

This new variety of *Taxodium distichum* is illustrated by the accompanying photographic prints in which:

1. The photograph at the top of the first sheet is a close-up showing the foliage and stem color of the new variety.

2. The photograph at the bottom of the first sheet is a close-up showing the typical variation in foliage shape of four different unnamed specimens of the species *Taxodium distichum.*

3. The photograph at the top of the second sheet shows the dense, upright and pyramidal growth habit of the new variety in an established landscape planting.

4. The photograph at the bottom of the second sheet shows the uniform growth habit and foliage color of a group of young three gallon plants.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Taxodium based on my observations made of 2 year old plants grown in 3 gallon containers in wholesale commercial production practices, in greenhouses, and in established landscape plantings in Loxley, Ala.

Distinctive Characteristics:

| Characteristic | *Taxodium distichum* | *Taxodium d.* 'Sofine' |
|---|---|---|
| Height (Mature) | 50–70' | 50–70' |
| Width (Mature) | 20–30' | 20–30' |
| Growth Habit | Globose to Pyramidal | Pyramidal |
| Leaf Length (on deciduous stems) | ⅛–¾" | ⅜–⅝" |
| Leaf Width (on deciduous stems) | 1/40–⅛" | 1/32–1/10" |
| Foliage Color (Immature) | Yellow-Green G. 144A-B, 146B-D | Yellow-Green G. 144A |

-continued

Distinctive Characteristics:

| Characteristic | *Taxodium distichum* | *Taxodium d.* 'Sofine' |
|---|---|---|
| Foliage Color (Mature) | Green G. 137A-D | Green G. 137C |
| Foliage Color (Fall) | Greyed-Orange G. 171B-C, 172A-C | Greyed-Orange G. 172C |

Taxodium 'Sofine' is similar to the parent species *Taxodium distichum*, however, in side-by-side comparisons conducted in Loxley, Ala., 'Sofine' produced a uniformly dense and pyramidal plant with uniform size and color. In the nursery industry *Taxodium distichum* is traditionally grown from seed which results in a tremendous amount of variation.

Classification

Botanic: *Taxodium distichum* 'Sofine'.
Parentage: Chance seedling of *Taxodium distichum.*
Commercial: Deciduous conifer.
Form: Dense, upright, pyramidal tree.
Height: 50–70'.
Width: 20–30'.

Growth rate: Fast under normal fertilization and moisture conditions. Mature height is 50–70' and width 20–30'. This is comparable to the parent species. Semi-hardwood cuttings taken in late spring through the summer produce rooted cuttings in three to four months in Loxley, Ala. Root development is vigorous and finely branched. From a rooted cutting, the new variety reaches a height of 4' and a spread of 20" in a period of two years, also in Loxley, Ala. The growth rate is normally about 2 to 3' per year while maintaing a dense habit due to the abundant branch development and short internode lengths.

Foliage: Alternate, linear, apiculate, deciduous of two types, one spirally arranged ⅛ to ½" long and 1/40 to 1/16" wide, incurved or appressed on persistent stems, the other flat or slightly curved, ⅜ to ⅝" long, 1/32 to 1/10" wide, spreading and 2-ranked on deciduous stems. Both the upper and lower surfaces of the leaves display the same color characteristics. Immature foliage is dull Yellow-Green Group 144A in spring and matures to Green Group 137C in summer. With the onset of cool weather in the fall, the leaf color changes to Greyed-Orange Group 172C and finally Greyed-Orange Group 165A just before falling.

In 1997 , the date of initial spring growth was March 25, in Loxley, Ala. After the initial spring flush there was almost continuous growth until fall, ending October 21, also in Loxley, Ala. This growth pattern was similar to the parent species. When grown in full sun, the internode length of 'Sofine' is ⅜" to 1" which is also similar to the parent species. As would be expected, either plant grown in the shade results in a taller, less dense plant with larger leaves.

The average length of terminal growth of the initial spring flush is about 10" for a plant in full sun and about 12" when grown in shade. There are usually 3 to 4 flushes of growth per year under ideal growing conditions in Loxley, Ala. Liners 8 to 10" tall planted in three gallon containers during the winter finish in the fall at about 3–4' tall and 2' wide. No triming is needed. *Taxodium distichum* seedlings grown under identical conditions were very inconsistent in vigor and color.

Buds (vegetative): Alternate, near tip of stem, rounded 1/16 to ⅛" long, 1/16 to ⅛" wide, Yelllow-Green Group 144A with overlapping scales. Smaller lateral buds 1/16" long and 1/16" wide are also present and produce leafy budless branches which are deciduous.

Stems: The single straight trunk produces stems of two kinds, persistent and deciduous. The persistent stems are glabrous, Greyed-Orange Group 164B and hold spirally-arranged leaves and deciduous stems. The deciduous stems are glabrous, 2–6" long and hold 40 to 125 leaves in 2-ranks and lack buds. The immature deciduous stems are Yellow-Green Group 144A in spring, maturing to Green Group 137C in summer and finally Greyed-Orange Group 165A before falling.

As the persistent stems mature into the winter they become Greyed-Orange Group 164A and rugose. After one or more years, the trunk becomes Greyed-Brown Group 199B, vertically fibrous and fissured with slightly exfoliating bark. The pith is solid and uniform.

Flowers: Monoecious, borne on mature previous season growth. The male cones are ⅛ to 3/16" in diameter, Green Group 137C, borne terminally in the fall on pendulous 4–5" long panicles that are conspicuous during the winter. There are 400–600 cones per panicle. Pollen is shed in March and April in Loxley, Ala. after which the male cones fall off. Female conelets mature with the initial spring growth and are found singly or in clusters of two or three. These conelets are subglobose, ⅛ to 3/16" in diameter, Yellow-Green Group 146C, comprising 8–10 spirally arranged peltate scales, each bearing two erect, basal ovules. There is a four to six week flowering period beginning in late March in Loxley, Ala. Flowers are not fragrant.

Fruit: Female cones are globose, ½ to 1¼" in diameter at maturity, on 1/16 to ⅛" long stalks, Yellow-Green Group 146A and resinous when young. Cones mature to Grey-Brown Group 199C from October to December and consist of 9 to 15 four-sided scales that break away irregularly after maturity. Seeds are Greyed-Orange Group 175B, one or two per scale, ½" long, irregular, triangle-shaped with a thick warty coat and projecting flanges. Each cone contains 10 to 30 seeds which are released during the winter.

Culture: Grows well in a wide range of conditions and tolerates sun to part shade. Grows in nearly any soil type from wet to dry and sand to clay. Responds well to mulching and medium applications of fertilizer; prefers ph 5.0 to 6.5. No pruning is needed. Cold hardiness and resistance to insects, disease, and drought are comparable to the parent species. Propagated with semi-hardwood cuttings in late spring through the summer. Cuttings taken at this time initate roots in 6 to 8 weeks and are well rooted in 3 to 4 months. The root system is fibrous and rapidly established.

Pests: None observed to date.

I claim:

1. A new and unique variety of *Taxodium distichum* plant named 'Sofine' as herein shown and described.

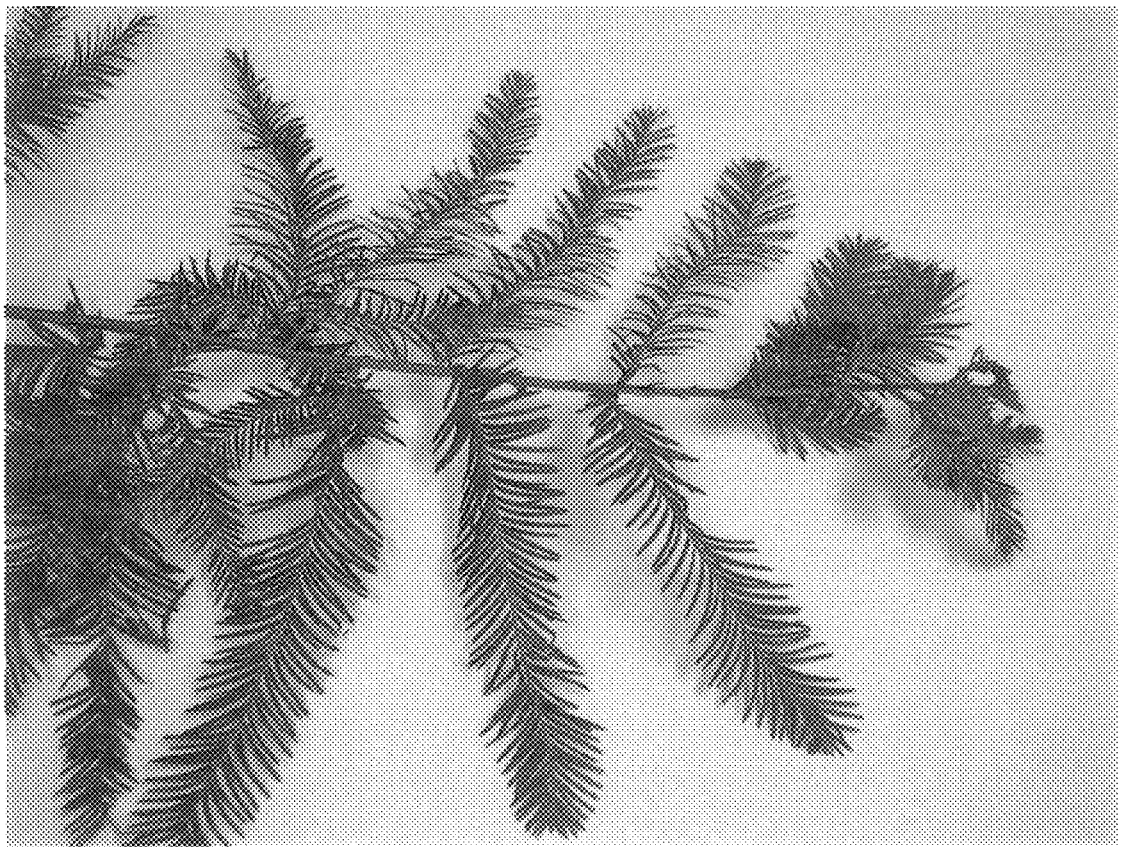
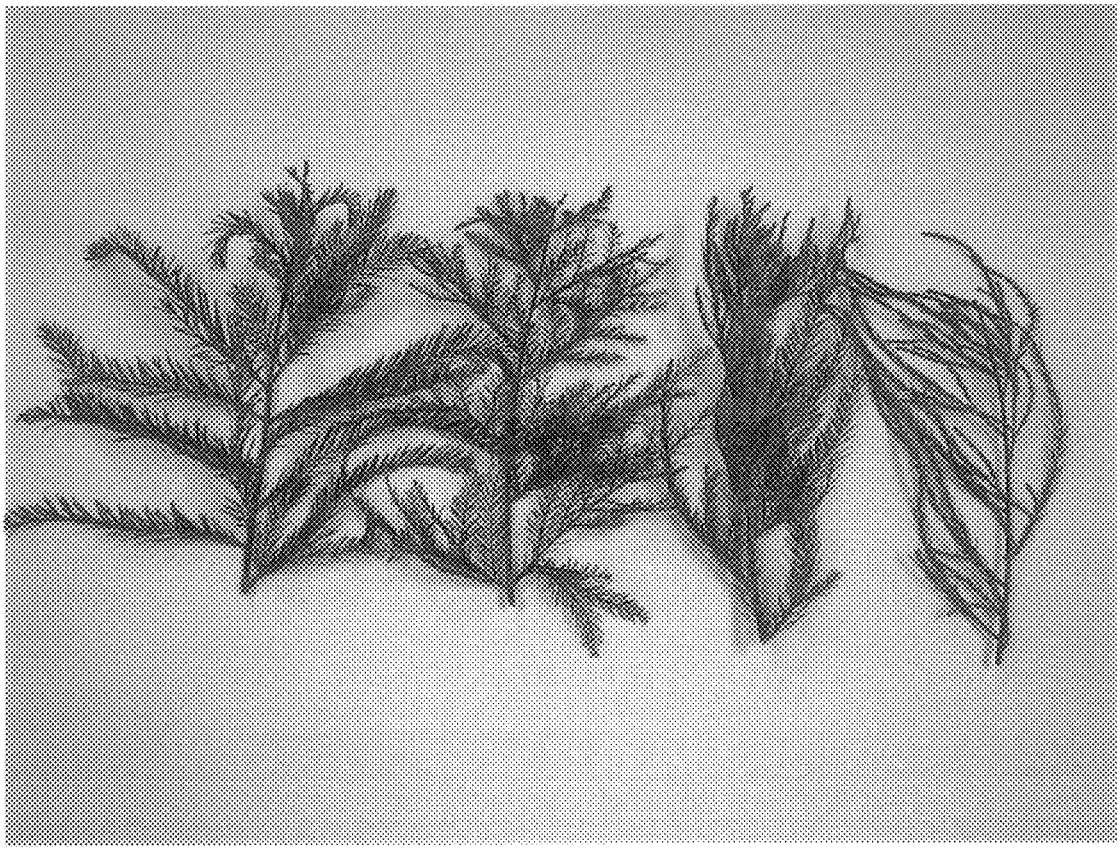

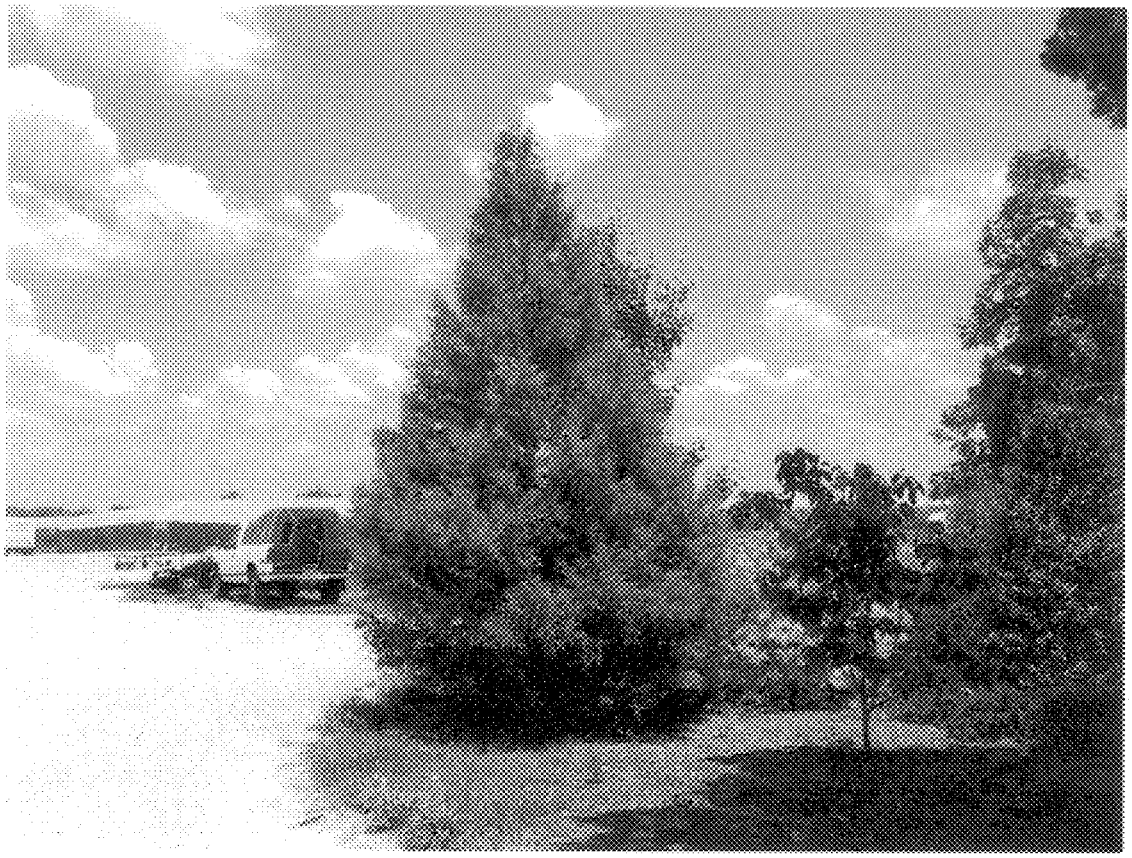
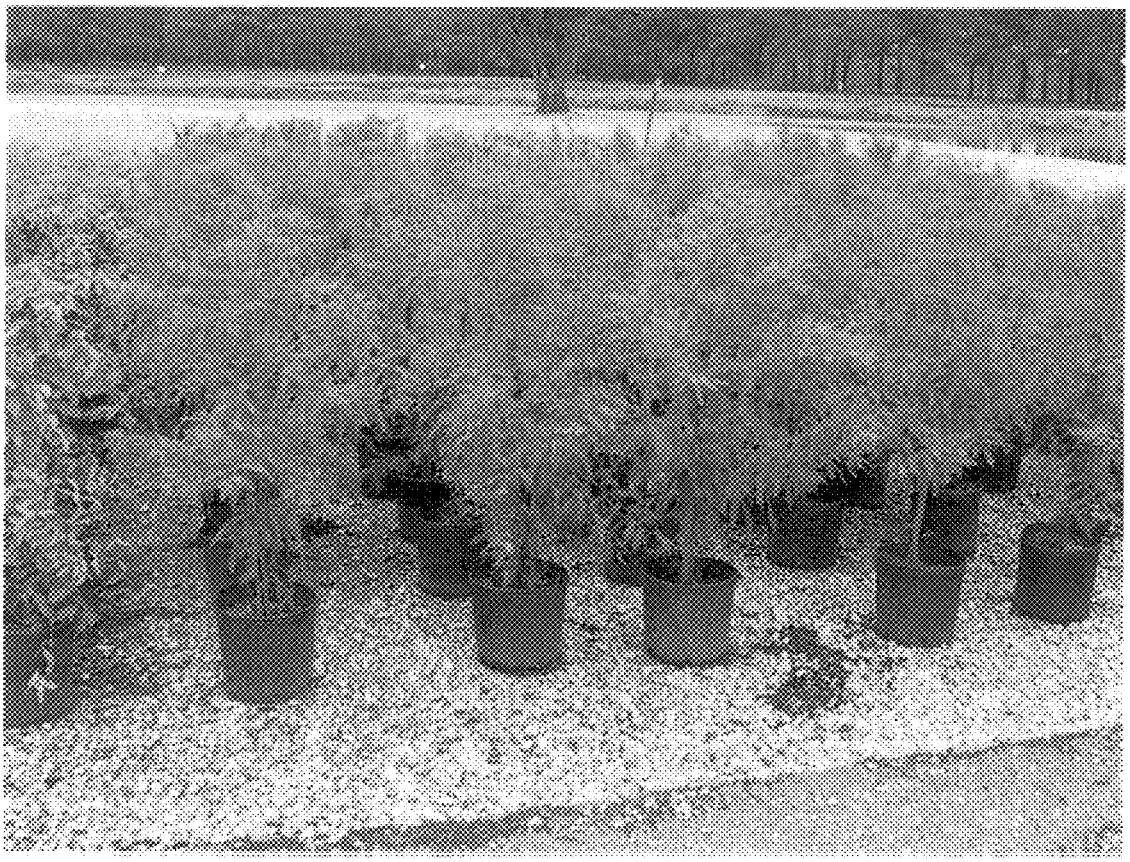

* * * * *